(12) United States Patent
Wright et al.

(10) Patent No.: US 8,179,418 B2
(45) Date of Patent: *May 15, 2012

(54) ROBOTIC BASED HEALTH CARE SYSTEM

(75) Inventors: Timothy C. Wright, Santa Barbara, CA (US); Fuji Lai, Goleta, CA (US); Marco Pinter, Santa Barbara, CA (US); Yulun Wang, Goleta, CA (US)

(73) Assignee: Intouch Technologies, Inc., Goleta, CA (US)

( * ) Notice: Subject to any disclaimer, the term of this patent is extended or adjusted under 35 U.S.C. 154(b) by 1052 days.

This patent is subject to a terminal disclaimer.

(21) Appl. No.: 12/082,953

(22) Filed: Apr. 14, 2008

(65) Prior Publication Data
US 2009/0259339 A1    Oct. 15, 2009

(51) Int. Cl.
*H04N 7/14* (2006.01)
*G05B 15/00* (2006.01)
*G06F 19/00* (2011.01)

(52) U.S. Cl. ....... 348/14.05; 283/54; 283/115; 318/567; 318/568.11; 434/262; 600/300; 700/245; 700/258; 700/259; 700/264; 705/2; 705/3; 715/719

(58) Field of Classification Search ............... 318/567, 318/568.11; 348/14.05; 600/300; 700/245, 700/258, 259, 264; 901/1; 283/54, 115; 434/262; 705/2, 3; 715/719
See application file for complete search history.

(56) References Cited

U.S. PATENT DOCUMENTS

| | | | |
|---|---|---|---|
| 4,413,693 A | 11/1983 | Derby | |
| 4,638,445 A | 1/1987 | Mattaboni | |
| 4,709,265 A | 11/1987 | Silverman et al. | |
| 4,803,625 A | 2/1989 | Fu et al. | |
| 4,875,172 A | 10/1989 | Kanayama | |
| 4,977,971 A | 12/1990 | Crane, III et al. | |
| 5,073,749 A | 12/1991 | Kanayama | |
| 5,084,828 A | 1/1992 | Kaufman et al. | |
| 5,130,794 A | 7/1992 | Ritchey | |
| 5,341,242 A | 8/1994 | Gilboa et al. | |

(Continued)

FOREIGN PATENT DOCUMENTS

CA    2289697 A1    11/1998

(Continued)

OTHER PUBLICATIONS

International Preliminary report on Patentability received for PCT Application No. PCT/US2009/036541, mailed on Oct. 28, 2010, 6 pages.

(Continued)

*Primary Examiner* — Gerald Gauthier

(74) *Attorney, Agent, or Firm* — Paul Evans

(57) ABSTRACT

A robotic system that can be used to treat a patient. The robotic system includes a mobile robot that has a camera. The mobile robot is controlled by a remote station that has a monitor. A physician can use the remote station to move the mobile robot into view of a patient. An image of the patient is transmitted from the robot camera to the remote station monitor. A medical personnel at the robot site can enter patient information into the system through a user interface. The patient information can be stored in a server. The physician can access the information from the remote station. The remote station may provide graphical user interfaces that display the patient information and provide both a medical tool and a patient management plan.

24 Claims, 8 Drawing Sheets

U.S. PATENT DOCUMENTS

| | | |
|---|---|---|
| 5,374,879 A | 12/1994 | Pin et al. |
| 5,441,047 A | 8/1995 | David et al. |
| 5,442,728 A | 8/1995 | Kaufman et al. |
| 5,462,051 A | 10/1995 | Oka et al. |
| 5,544,649 A | 8/1996 | David et al. |
| 5,553,609 A | 9/1996 | Chen et al. |
| 5,572,229 A | 11/1996 | Fisher |
| 5,652,849 A * | 7/1997 | Conway et al. ............... 715/719 |
| 5,762,458 A | 6/1998 | Wang et al. |
| 5,786,846 A | 7/1998 | Hiroaki |
| 5,802,494 A | 9/1998 | Kuno |
| 5,917,958 A | 6/1999 | Nunally et al. |
| 927,423 A | 7/1999 | Wada et al. |
| 5,959,423 A | 9/1999 | Nakanishi et al. |
| 5,966,130 A | 10/1999 | Benman, Jr. |
| 6,133,944 A | 10/2000 | Braun et al. |
| 6,135,228 A | 10/2000 | Asada et al. |
| 6,211,903 B1 | 4/2001 | Bullister |
| 6,219,587 B1 | 4/2001 | Ahlin et al. |
| 6,232,735 B1 * | 5/2001 | Baba et al. .................... 318/567 |
| 6,233,504 B1 | 5/2001 | Das et al. |
| 6,256,556 B1 * | 7/2001 | Zenke ............................ 700/245 |
| 6,259,806 B1 | 7/2001 | Green |
| 6,292,713 B1 * | 9/2001 | Jouppi et al. .................. 700/245 |
| 6,304,050 B1 * | 10/2001 | Skaar et al. ............. 318/568.11 |
| 6,321,137 B1 | 11/2001 | De Smet |
| 6,325,756 B1 | 12/2001 | Webb et al. |
| 6,330,493 B1 | 12/2001 | Takahashi et al. |
| 6,346,950 B1 | 2/2002 | Jouppi |
| 6,369,847 B1 | 4/2002 | James et al. |
| 6,430,471 B1 * | 8/2002 | Kintou et al. ................. 700/245 |
| 6,430,475 B2 | 8/2002 | Okamoto et al. |
| 6,438,457 B1 | 8/2002 | Yokoo et al. |
| 6,463,361 B1 | 10/2002 | Wang et al. |
| 6,466,844 B1 | 10/2002 | Ikeda et al. |
| 6,491,701 B2 | 12/2002 | Tierney et al. |
| 6,496,099 B2 | 12/2002 | Wang et al. |
| 6,507,773 B2 * | 1/2003 | Parker et al. .................. 700/258 |
| 6,522,906 B1 | 2/2003 | Salisbury et al. |
| 6,532,404 B2 | 3/2003 | Colens |
| 6,535,182 B2 | 3/2003 | Stanton |
| 6,535,793 B2 * | 3/2003 | Allard ........................... 700/259 |
| 6,540,039 B1 | 4/2003 | Yu et al. |
| 6,543,899 B2 | 4/2003 | Covannon et al. |
| 6,549,215 B2 | 4/2003 | Jouppi |
| 6,604,019 B2 | 8/2003 | Ahlin et al. |
| 6,646,677 B2 | 11/2003 | Noro et al. |
| 6,684,129 B2 | 1/2004 | Salisbury et al. |
| 6,691,000 B2 | 2/2004 | Nagai et al. |
| 6,728,599 B2 | 4/2004 | Wang et al. |
| 6,781,606 B2 | 8/2004 | Jouppi |
| 6,784,916 B2 | 8/2004 | Smith |
| 6,799,065 B1 | 9/2004 | Niemeyer |
| 6,799,088 B2 | 9/2004 | Wang et al. |
| 6,804,656 B1 | 10/2004 | Rosenfeld et al. |
| 6,836,703 B2 | 12/2004 | Wang et al. |
| 6,839,612 B2 | 1/2005 | Sanchez et al. |
| 6,840,904 B2 | 1/2005 | Goldberg |
| 6,845,297 B2 | 1/2005 | Allard |
| 6,852,107 B2 | 2/2005 | Wang et al. |
| 6,871,117 B2 | 3/2005 | Wang et al. |
| 6,879,879 B2 | 4/2005 | Jouppi et al. |
| 6,892,112 B2 | 5/2005 | Wang et al. |
| 6,895,305 B2 | 5/2005 | Lathan et al. |
| 6,914,622 B1 | 7/2005 | Smith et al. |
| 6,925,357 B2 | 8/2005 | Wang et al. |
| 6,995,664 B1 | 2/2006 | Darling |
| 7,115,102 B2 | 10/2006 | Abbruscato |
| 7,123,285 B2 | 10/2006 | Smith et al. |
| 7,129,970 B2 | 10/2006 | James et al. |
| 7,151,982 B2 | 12/2006 | Liff et al. |
| 7,154,526 B2 | 12/2006 | Foote et al. |
| 7,155,306 B2 | 12/2006 | Haitin et al. |
| 7,156,809 B2 | 1/2007 | Quy |
| 7,161,322 B2 | 1/2007 | Wang et al. |
| 7,164,969 B2 * | 1/2007 | Wang et al. ................... 700/245 |
| 7,174,238 B1 | 2/2007 | Zweig |
| 7,184,559 B2 | 2/2007 | Jouppi |
| 7,188,000 B2 | 3/2007 | Chiappetta et al. |
| 7,256,708 B2 | 8/2007 | Rosenfeld |
| 7,262,573 B2 | 8/2007 | Wang et al. |
| 7,289,883 B2 * | 10/2007 | Wang et al. ................... 700/245 |
| 7,593,030 B2 * | 9/2009 | Wang et al. ................. 348/14.05 |
| 7,761,185 B2 * | 7/2010 | Wang et al. ................... 700/259 |
| 8,116,910 B2 * | 2/2012 | Walters et al. ................ 700/259 |
| 2001/0010053 A1 | 7/2001 | Ben-Shachar et al. |
| 2001/0037163 A1 | 11/2001 | Allard |
| 2001/0054071 A1 | 12/2001 | Loeb |
| 2002/0027597 A1 | 3/2002 | Sachau |
| 2002/0057279 A1 | 5/2002 | Jouppi |
| 2002/0058929 A1 | 5/2002 | Green |
| 2002/0063726 A1 | 5/2002 | Jouppi |
| 2002/0120362 A1 | 8/2002 | Lathan et al. |
| 2002/0130950 A1 | 9/2002 | James et al. |
| 2002/0141595 A1 | 10/2002 | Jouppi |
| 2002/0183894 A1 | 12/2002 | Wang et al. |
| 2003/0048481 A1 | 3/2003 | Kobayashi |
| 2003/0050733 A1 | 3/2003 | Wang et al. |
| 2003/0060808 A1 | 3/2003 | Wilk |
| 2003/0100892 A1 | 5/2003 | Morley et al. |
| 2003/0114962 A1 | 6/2003 | Niemeyer |
| 2003/0135203 A1 | 7/2003 | Wang et al. |
| 2003/0144579 A1 | 7/2003 | Buss |
| 2003/0144649 A1 | 7/2003 | Ghodoussi et al. |
| 2003/0151658 A1 | 8/2003 | Smith |
| 2003/0199000 A1 | 10/2003 | Valkirs et al. |
| 2003/0220541 A1 | 11/2003 | Salisbury et al. |
| 2004/0019406 A1 | 1/2004 | Wang et al. |
| 2004/0088077 A1 | 5/2004 | Jouppi et al. |
| 2004/0117065 A1 | 6/2004 | Wang et al. |
| 2004/0143421 A1 | 7/2004 | Wang et al. |
| 2004/0162637 A1 | 8/2004 | Wang et al. |
| 2004/0167666 A1 | 8/2004 | Wang et al. |
| 2004/0167668 A1 | 8/2004 | Wang et al. |
| 2004/0174129 A1 | 9/2004 | Wang et al. |
| 2004/0215490 A1 | 10/2004 | Duchon et al. |
| 2005/0021182 A1 | 1/2005 | Wang et al. |
| 2005/0021183 A1 | 1/2005 | Wang et al. |
| 2005/0021187 A1 | 1/2005 | Wang et al. |
| 2005/0024485 A1 | 2/2005 | Castles et al. |
| 2005/0027794 A1 | 2/2005 | Decker |
| 2005/0028221 A1 | 2/2005 | Liu et al. |
| 2005/0035862 A1 | 2/2005 | Wildman et al. |
| 2005/0038416 A1 | 2/2005 | Wang et al. |
| 2005/0038564 A1 | 2/2005 | Burick et al. |
| 2005/0052527 A1 | 3/2005 | Remy et al. |
| 2005/0065438 A1 | 3/2005 | Miller |
| 2005/0065659 A1 | 3/2005 | Tanaka et al. |
| 2005/0110867 A1 | 5/2005 | Schultz |
| 2005/0204438 A1 | 9/2005 | Wang et al. |
| 2006/0007943 A1 | 1/2006 | Fellman |
| 2006/0013263 A1 | 1/2006 | Fellman |
| 2006/0029065 A1 | 2/2006 | Fellman |
| 2006/0047365 A1 | 3/2006 | Ghodoussi et al. |
| 2006/0052676 A1 * | 3/2006 | Wang et al. ................... 600/300 |
| 2006/0064212 A1 | 3/2006 | Thorne |
| 2006/0082642 A1 | 4/2006 | Wang et al. |
| 2006/0098573 A1 | 5/2006 | Beer et al. |
| 2006/0104279 A1 | 5/2006 | Fellman et al. |
| 2006/0142983 A1 | 6/2006 | Sorensen et al. |
| 2006/0173712 A1 | 8/2006 | Joubert |
| 2006/0259193 A1 | 11/2006 | Wang et al. |
| 2007/0064092 A1 | 3/2007 | Sandbeg et al. |
| 2007/0120965 A1 | 5/2007 | Sandberg et al. |
| 2007/0122783 A1 * | 5/2007 | Habashi ........................ 434/262 |
| 2007/0192910 A1 | 8/2007 | Vu et al. |
| 2007/0198128 A1 | 8/2007 | Ziegler et al. |
| 2007/0199108 A1 | 8/2007 | Angle et al. |
| 2007/0273751 A1 | 11/2007 | Sachau |
| 2008/0281467 A1 * | 11/2008 | Pinter ........................... 700/245 |
| 2009/0055023 A1 * | 2/2009 | Walters et al. ................ 700/259 |
| 2009/0240371 A1 * | 9/2009 | Wang et al. ................... 700/259 |
| 2009/0259339 A1 * | 10/2009 | Wright et al. ................. 700/264 |
| 2010/0191375 A1 * | 7/2010 | Wright et al. ................. 700/259 |
| 2011/0172822 A1 * | 7/2011 | Ziegler et al. ................. 700/259 |

FOREIGN PATENT DOCUMENTS

| | | |
|---|---|---|
| EP | 0981905 B1 | 1/2002 |
| JP | 07-257422 A | 10/1995 |
| JP | 08-084328 A | 3/1996 |
| JP | 2000-032319 A | 1/2000 |
| JP | 2002-046088 A | 2/2002 |
| JP | 2002-305743 A | 10/2002 |

OTHER PUBLICATIONS

F. Ando et al., "A Multimedia Self-service Terminal with Conferencing Functions", 1995, IEEE, pp. 357-362.
Bar-Cohen et al., Virtual reality robotic telesurgery simulations using MEMICA haptic system, Mar. 5, 2001, Internet, pp. 1-7.
Bauer, Jeffrey C., "Service Robots in Health Care: The Evolution of Mechanical Solutions to Human Resource Problems", Jun. 2003.
Bauer, John et al., "Remote telesurgical mentoring: feasibility and efficacy", 2000, IEEE, pp. 1-9.
Breslow, Michael J., MD et al., "Effect of a multiple-site intensive care unit telemedicine program on clinical and economic outcome: An alternative paradigm for intensivist staffing", Critical Care Med, Jan. 2004, vol. 32, No. 1, pp. 31-38.
Brooks, Rodney, Abstracts from Flesh & Machines, How Robots Will Change Us, "Remote Presence", p. 131-147, Feb. 2002.
Celi et al., "The eICU: It's not just telemedicine", Critical Care Medicine, vol. 29, No. 8 (Supplement), Aug. 2001.
Cleary et al., "State of the art in surgical robotics: Clinical applications and technology challenges", Feb. 24, 2002 Internet, pp. 1-26.
CNN, Floating 'droids' to roam space corridors of the future, Jan. 12, 2000, Internet, pp. 1-4.
CNN.com/Technology, Paging R.Robot: Machine helps doctors with patients, Sep. 30, 2003, Internet, 1-3.
Davies, "Robotics in Minimally Invasive Surgery", 1995, Internet, pp. 5/1-5/2.
DiGiorgio, James, "Is Your Emergency Department of the 'Leading Edge'?", 2005, Internet, pp. 1-4.
Elhajj et al., "Supermedia in Internet-based telerobotic operations", 2001, Internet, pp. 1-14.
Fetterman, Videoconferencing over the Internet, 2001, Internet, pp. 1-8.
Goldberg et al., "Collaborative Teleoperation via the Internet", IEEE International Conference on Robotics and Automation, Apr. 2000, San Francisco, California.
Goldman, Lea, "Machine Dreams", Entrepreneurs, Forbes, May 27, 2002.
Gump, Michael D., "Robot Technology Improves VA Pharmacies", 2001, Internet, pp. 1-3.
Harmo et al., "Moving Eye—Interactive Telepresence Over Internet With a Ball Shaped Mobile Robot", 2000.
Hees, William P., "Communications Design for a Remote Presence Robot", Jan. 14, 2002.
F.A. Candelas Herias et al., "Flexible virtual and remote laboratory for teaching Robotics", FORMATEX 2006, Proc. Advance in Control Education, Madrid, Spain, Jun. 21-23, 2006.
Ishihara, Ken et al., "Intelligent Microrobot DDS (Drug Delivery System) Measured and Controlled by Ultrasonics", Nov. 11-Mar. 5, 1991, IEEE/RSJ, pp. 1145-1150, vol. 2.
Johanson, Supporting video-mediated communication over the Internet, Chalmers University of Technology, Dept of Computer Engineering, Gothenburg, Sweden, 2003.
Jouppi, et al., :Mutually-lmmersive Audio Telepresence, Audio Engineering Society Convention Paper, presented at 113th Convention Oct. 2002.
Jouppi, Norman P., "First Steps Towards Mutually-Immersive Mobile Telepresence", CSCW '02, Nov. 16-20, 2002, New Orleans LA.
Kanehiro, Fumio et al., Virtual Humanoid Robot Platform to Develop Controllers of Real Humanoid Robots without Porting, 2001, IEEE, pp. 3217-3276.
Lim, Hun-ok et al., Control to Realize Human-like Walking of a Biped Humanoid Robot, IEEE 2000, pp. 3271-3276.
Linebarger, John M. et al., "Concurrency Control Mechanisms for Closely Coupled Collaboration in Multithreaded Virtual Environments", Presence, Special Issue on Advances in Collaborative VEs (2004).
Loeb, Gerald, "Virtual Visit: Improving Communication for Those Who Need It Most", 2001.
Mack, "Minimally invasive and robotic surgery", 2001, Internet IEEE, pp. 568-572.
Martin, Anya, "Days Ahead", Assisted Living Today, vol. 9, Nov./Dec. 2002, pp. 19-22.
McCardle et al., "The challenge of utilizing new technology in design education", 2000 Internet, pp. 122-127.
"More Online Robots, Robots that Manipulate", Internet, http://ford.ieor.berkeley.edu/ir/robots_a2.html, Feb. 2007.
Nakajima et al., "A Multimedia Teleteaching System sing an Electronic Whiteboard for Two-Way Communication of Motion Videos and Chalkboards", 1993, IEEE, pp. 436-441.
Ogata et al., "Development of Emotional Communication Robot: WAMOEBA-2r—Esperimental evaluation . . . ", 2000 IEEE, pp. 175-180.
Ojha, Anad, "An application of Virtual Reality in Rehabilitation", Jan. 1994, IEEE, pp. 4-6.
Paulos et al., "A World Wide Web Telerobotic Remote Environment Browser", http://vive.cs.berkeley.edu/capek, 1995.
Paulos, Eric John, "Personal Tele-Embodiment", Fall 2001.
Paulos, et al. , "Ubiquitous Tele-embodiment: Applications and Implications", International Journal of Human Computer Studies, Jun. 1997, vol. 46, No. 6, pp. 861-877.
Pin et al., "A New Family of Omnidirectional and Holonomic Wheeled Platforms for Mobile Robots", IEEE, vol. 10, No. 4, Aug. 1994.
Robot Hardware Mobile Robotics Research Group, Edinburgh, "Mobile Robotics Research Group", 2000 Internet, pp. 1-2.
Roy et al., "Towards Personal Service Robots for the Elderly", Internet, Mar. 7, 2002.
Salemi et al, "MILO: Personal robot platform", 2005, Internet, pp. 1-6.
Sandt, Frederic et al., "Perceptions for a Transport Robot in Public Environments", 1997, IROS '97.
Shimoga et al., Touch and force reflection for telepresence surgery, 1994, IEEE, pp. 1049-1050.
Stephenson, Gary, "Dr. Robot Tested at Hopkins", Aug. 5, 2003, Internet, pp. 1-2.
Stoianovici et al., "Robotic Tools for Minimally Invasive Urologic Surgery", Dec. 2002, Internet, 1-17.
Tendick et al., "Human-Machine Interfaces for Minimally Invasive Surgery", 1997, IEEE, pp. 2771-2776.
Thrun et al, "Probabilistic Algorithms and the Interactive Museum Tour-Guide Robot Minerva", 2000, Internet pp. 1-35.
Tzafestas, et al., "VR-based Teleoperation of a Mobile Robotic Assistant: Progress Report", 2000, Internet, pp. 1-23.
Urquhart, Kim, "InTouch's robotic Companion 'beams up' healthcare experts", Medical Device Daily, vol. 7, No. 39, Feb. 27, 2003, p. 1, 4.
Weiss et al., Telework and video-mediated communication: Importance of real-time, interactive communication for workers with disabilities, 1999, Internet, pp. 1-4.
Yamasaki et al., Applying Personal Robots and Active Interface to Video Conference Systems, 1995, Internet, pp. 243-248.
Yong et al., "Robot task execution with telepresence using virtual reality technology", 1998, Internet, pp. 1-9.
Zipperer, Lorri, "Robotic dispensing system", 1999, Internet, pp. 1-2.
Zorn, Benjamin G., "Ubiquitous Telepresence", http://www.cs.colorado.edu/~zorn/ut/vision/vision.htrnl, Mar. 5, 1996.

* cited by examiner

ROBOTIC BASED HEALTH CARE SYSTEM

BACKGROUND OF THE INVENTION

1. Field of the Invention

The subject matter disclosed generally relates to the fields of health care and robotics.

2. Background Information

The increasing complexity of healthcare and resulting clinical specialization is causing fragmentation of care compromising patient safety and hospital efficiency. There is the need for availability of clinical specialist expertise to cut across time and space as well as the need for standardization and dissemination of best practices and protocols for optimal quality of care for citizens regardless of where they live.

The need for clinical specialist expertise is especially acute in the diagnosis and treatment of stroke whereby immediate access to expertise and interdisciplinary communication and collaboration is key. Stroke is the second cause of death worldwide and the third leading cause of death in the United States. Recent development of several new therapies including tPA and neuro-endovascular procedures such as coiling offers real hope to change the once bleak prognosis for stroke victims. However, these new therapies are not widely available. Nationally, fewer than 5% of stroke victims are receiving any sort of treatment compared with leading stroke centers where approximately 25% of victims are treated. Most community hospitals do not have the basic patient assessment capability in place on a 24/7 basis nor have they established the appropriate ED treatment protocols. Additionally, only a very few hospitals have the specialists on staff required for neuro-endovascular procedures. Therefore stroke patients are either immediately transferred without proper evaluation or go untreated.

A major challenge in delivering stroke care relates to the time elements of stroke. The adage "time is brain" is often heard. The challenge is to get the right expertise and treatment to the patient at the right time. This encompasses the-entire continuum of care from emergency medical services and ambulance transport to evaluation in the ED and definitive treatment. Some stroke care guidelines have been established by the National Institute for Neurological Disorders and Stroke (NINDS). For example, the guidelines suggest getting a patient with symptoms of stroke to stroke expertise (e.g. neurologist, stroke team activation) within fifteen minutes. The use of the word "expertise" here is significant in that the expert need not be physically present next to the patient but could be made available through a consult, for example, over the phone.

BRIEF SUMMARY OF THE INVENTION

A robotic system that includes a mobile robot that has a camera. The system also includes a user interface that allows medical information to be entered by a user. The mobile robot is coupled to a remote station that can control movement of the robot. The remote station includes a monitor that is coupled to the mobile robot camera and displays the medical information.

BRIEF DESCRIPTION OF THE DRAWINGS

FIG. 6 is a graphical user interface at the remote station;

FIG. 7 is a graphical user interface when a NIHSS tab is selected;

DETAILED DESCRIPTION

Disclosed is a robotic system that can be used to treat a patient. The robotic system includes a mobile robot that has a camera. The mobile robot is controlled by a remote station that has a monitor. A physician can use the remote station to move the mobile robot into view of a patient. An image of the patient is transmitted from the robot camera to the remote station monitor. A medical personnel at the robot site can enter patient information into the system through a user interface. The patient information can stored in a server. The physician can access the information from the remote station. The remote station may provide graphical user interfaces that display the patient information and provide a medical tool. By way of example, the remote station may present to the user a NIHSS questionnaire to determine the severity of a stroke. The graphical user interfaces may include an interface that provides a patient management plan such as a calculated dosage. The medical tool and dosage can be transmitted to the user interface so that this information can be viewed by medical personnel in physical proximity to the patient. The system allows a clinical specialist to remotely observe and treat a patient. This is particularly advantageous when treating stroke patients, where time is critical.

Figure 1:
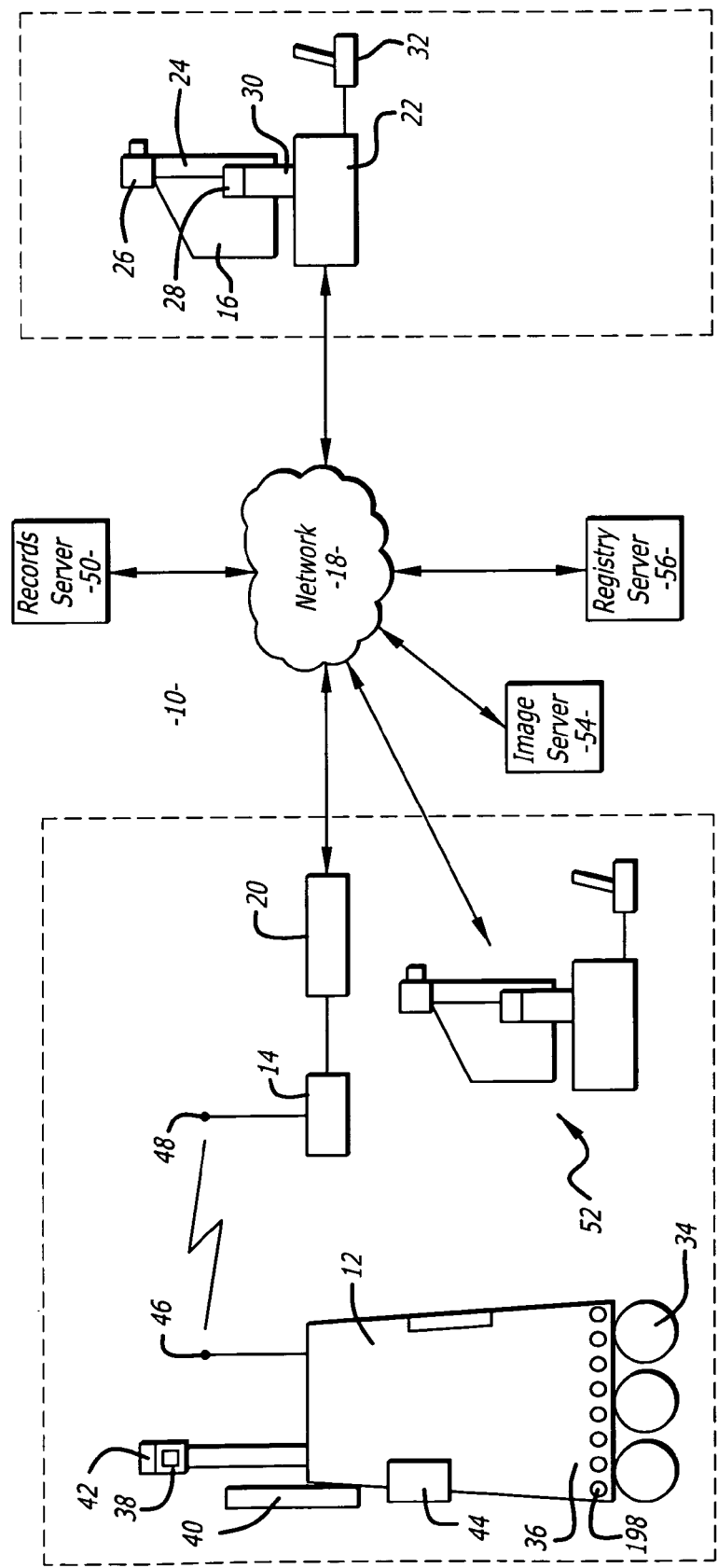
FIG. 1 is an illustration of a robotic system.

Referring to the drawings more particularly by reference numbers, FIG. 1 shows a robotic system 10. The robotic system 10 includes one or more robots 12. Each robot 12 has a base station 14. The robot 12 is coupled to a remote control station 16. The remote control station 16 may be coupled to the base station 14 through a network 18. By way of example, the network 18 may be either a packet switched network such as the Internet, or a circuit switched network such has a Public Switched Telephone Network (PSTN) or other broadband system. The base station 14 may be coupled to the network 18 by a modem 20 or other broadband network interface device. By way of example, the base station 14 may be a wireless router. Alternatively, the robot 12 may have a direct connection to the network thru for example a satellite.

The remote control station 16 may include a computer 22 that has a monitor 24, a camera 26, a microphone 28 and a speaker 30. The computer 22 may also contain an input device 32 such as a joystick or a mouse. The control station 16 is typically located in a place that is remote from the robot 12. Although only one remote control station 16 is shown, the system 10 may include a plurality of remote stations. In general any number of robots 12 may be controlled by any number of remote stations 16 or other robots 12. For example, one remote station 16 may be coupled to a plurality of robots 12, or one robot 12 may be coupled to a plurality of remote stations 16, or a plurality of robots 12.

Each robot 12 includes a movement platform 34 that is attached to a robot housing 36. The robot 12 may also have a camera 38, a monitor 40, a microphone(s) 42 and a speaker(s) 44. The microphone 42 and speaker 30 may create a stereophonic sound. The robot 12 may also have an antenna 46 that is wirelessly coupled to an antenna 48 of the base station 14. The system 10 allows a user at the remote control station 16 to move the robot 12 through operation of the input device 32.

The robot camera 38 is coupled to the remote monitor 24 so that a user at the remote station 16 can view a patient. Likewise, the robot monitor 40 is coupled to the remote camera 26 so that the patient can view the user. The microphones 28 and 42, and speakers 30 and 44, allow for audible communication between the patient and the user.

The remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

The system 10 may include a records server 50 that can be accessed through the network 18. Patient information can be provided to the server 50 through a user interface 52. The user interface 52 may or may not be in close proximity to the robot 12. For example, the user interface may be a computer located at a nurses station where information is entered when a patient checks into a facility. The robot 12 can be moved into view of the patient so that patient information can be entered into the system while a physician is viewing the patient through the robot camera. The physician can remotely move the robot to obtain different viewing angles of the patient. The user interface 52 may be a separate computer terminal. Alternatively, the user interface 52 may be integral with the robot. For example, the robot monitor may be a touch screen that allows a user to enter data into the system through the robot 12. The server 50 may contain other medical records of a patient such as written records of treatment, patient history, medication information, x-rays, EKGs, laboratory results, physician notes, etc.

The system 10 may also include an image server 54 and a registry server 56. The image server 54 may include medical images. For example, the medical images may include CT scans of a patient's brain. The images can be downloaded to one of the remote stations 14 through the network 18. The registry server 56 may store historical data on patients. The historical data can be downloaded to a remote computer 16 through the network 18.

Figure 2:
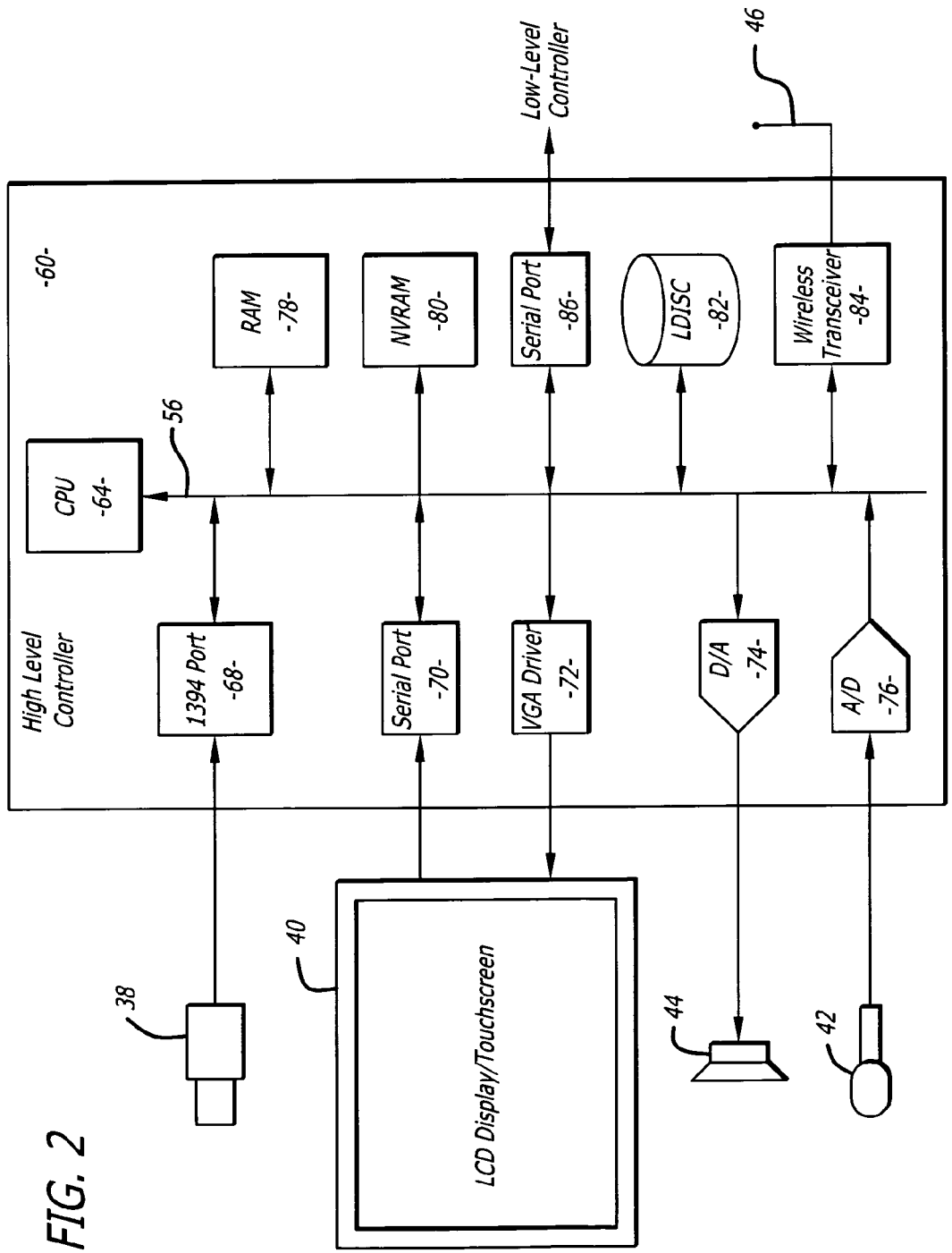
FIG. 2 is a schematic of an electrical system of a robot.
Figure 3:
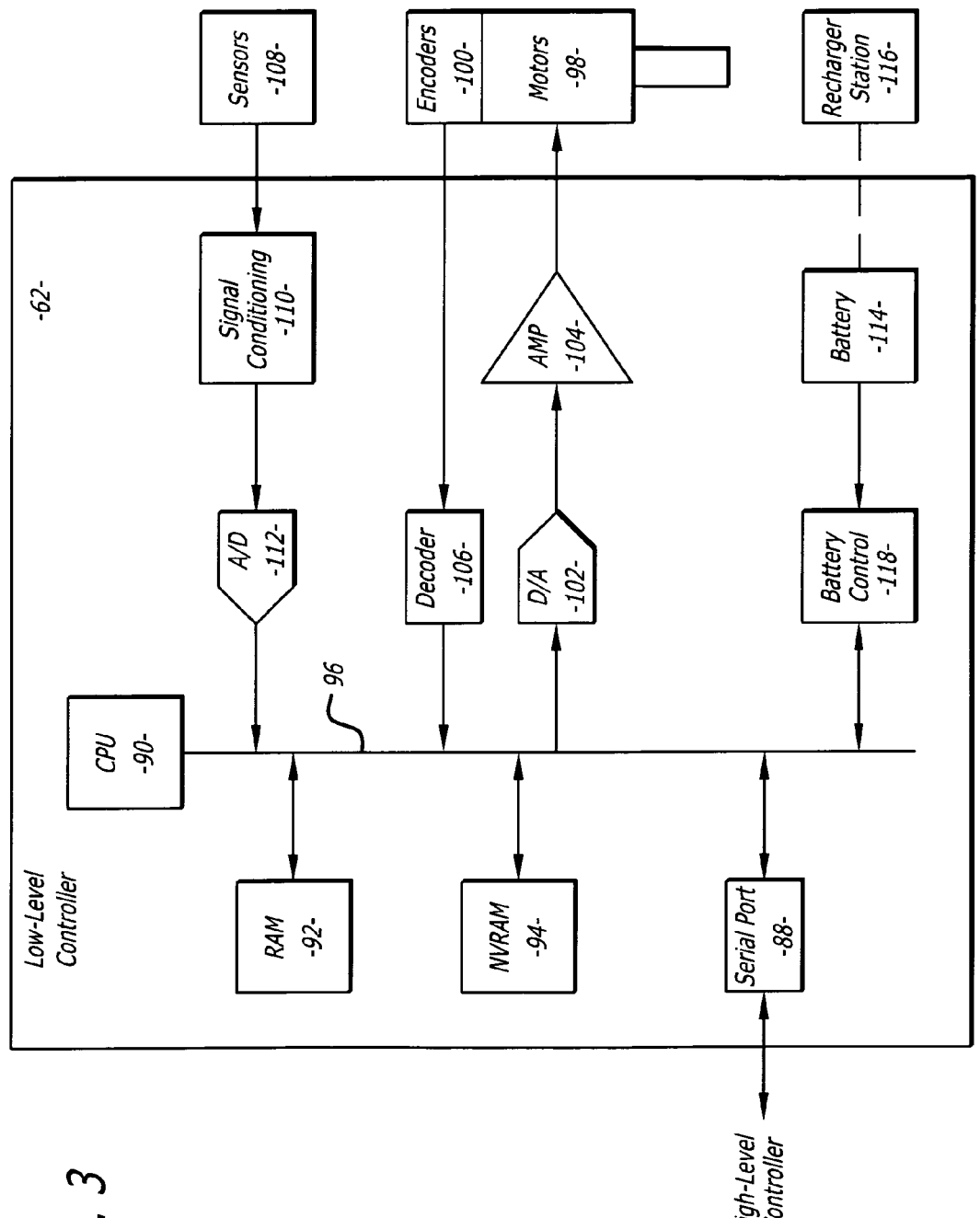
FIG. 3 is a further schematic of the electrical system of the robot.

FIGS. 2 and 3 show an embodiment of a robot 12. Each robot 12 may include a high level control system 60 and a low level control system 62. The high level control system 60 may include a processor 64 that is connected to a bus 66. The bus is coupled to the camera 38 by an input/output (I/O) port 68, and to the monitor 40 by a serial output port 70 and a VGA driver 72. The monitor 40 may include a touchscreen function that allows a user to enter input by touching the monitor screen.

The speaker 44 is coupled to the bus 56 by a digital to analog converter 74. The microphone 42 is coupled to the bus 66 by an analog to digital converter 76. The high level controller 60 may also contain random access memory (RAM) device 78, a non-volatile RAM device 80 and a mass storage device 82 that are all coupled to the bus 72. The mass storage device 82 may contain medical files of the patient that can be accessed by the user at the remote control station 16. For example, the mass storage device 82 may contain a picture of the patient. The user, particularly a health care provider, can recall the old picture and make a side by side comparison on the monitor 24 with a present video image of the patient provided by the camera 38. The robot antennae 46 may be coupled to a wireless transceiver 84. By way of example, the transceiver 84 may transmit and receive information in accordance with IEEE 802.11b.

The controller 64 may operate with a LINUX OS operating system. The controller 64 may also operate MS WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 60 operates to control communication between the robot 12 and the remote control station 16.

The high level controller 60 may be linked to the low level controller 62 by a serial port 88. The low level controller 62 includes a processor 90 that is coupled to a RAM device 92 and non-volatile RAM device 94 by a bus 96. Each robot 12 contains a plurality of motors 98 and motor encoders 100. The encoders 100 provide feedback information regarding the output of the motors 98. The motors 98 can be coupled to the bus 96 by a digital to analog converter 102 and a driver amplifier 104. The encoders 100 can be coupled to the bus 86 by a decoder 106. Each robot 12 may have a number of proximity sensors 108 (see also FIG. 1). The sensors 108 can be coupled to the bus 96 by a signal conditioning circuit 110 and an analog to digital converter 112.

The low level controller 62 runs software routines that mechanically actuate the robot 12. For example, the low level controller 62 provides instructions to actuate the movement platform to move the robot 12. The low level controller 62 may receive movement instructions from the high level controller 60. The movement instructions may be received as movement commands from the remote control station or another robot. Although two controllers are shown, it is to be understood that each robot 12 may have one controller, or more than two controllers, controlling the high and low level functions.

The various electrical devices of each robot 12 may be powered by a battery(ies) 114. The battery 114 may be recharged by a battery recharger station 116 (see also FIG. 1). The low level controller 62 may include a battery control circuit 118 that senses the power level of the battery 114. The low level controller 62 can sense when the power falls below a threshold and then send a message to the high level controller 60.

The system may be the same or similar to a robotic system provided by the assignee InTouch Technology, Inc. of Santa Barbara, Calif. under the name RP-7, which is hereby incorporated by reference. The system may also be the same or similar to the system disclosed in U.S. Pat. No. 7,292,912, which is hereby incorporated by reference.

Figure 4:
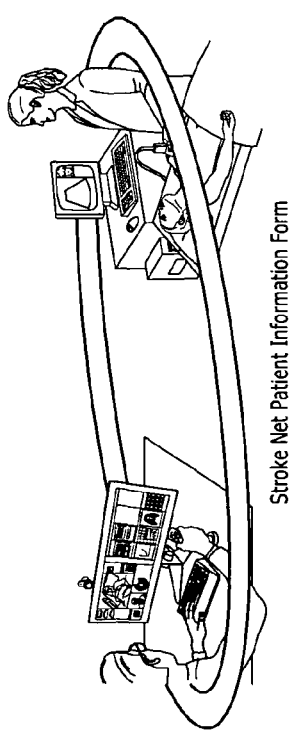
FIG. 4 is a graphical user interface of a user interface.

FIG. 4 shows a graphical user interface 150 provided at the user interface 52. The graphical user interface 150 includes a plurality of data fields 152 that can be filled by the user. The data fields 152 can request patient information such as name, age, etc. The data fields may also include request for medical data such as heart rate, glucose level and blood pressure ("SBP" and "DBP").

Figure 5:
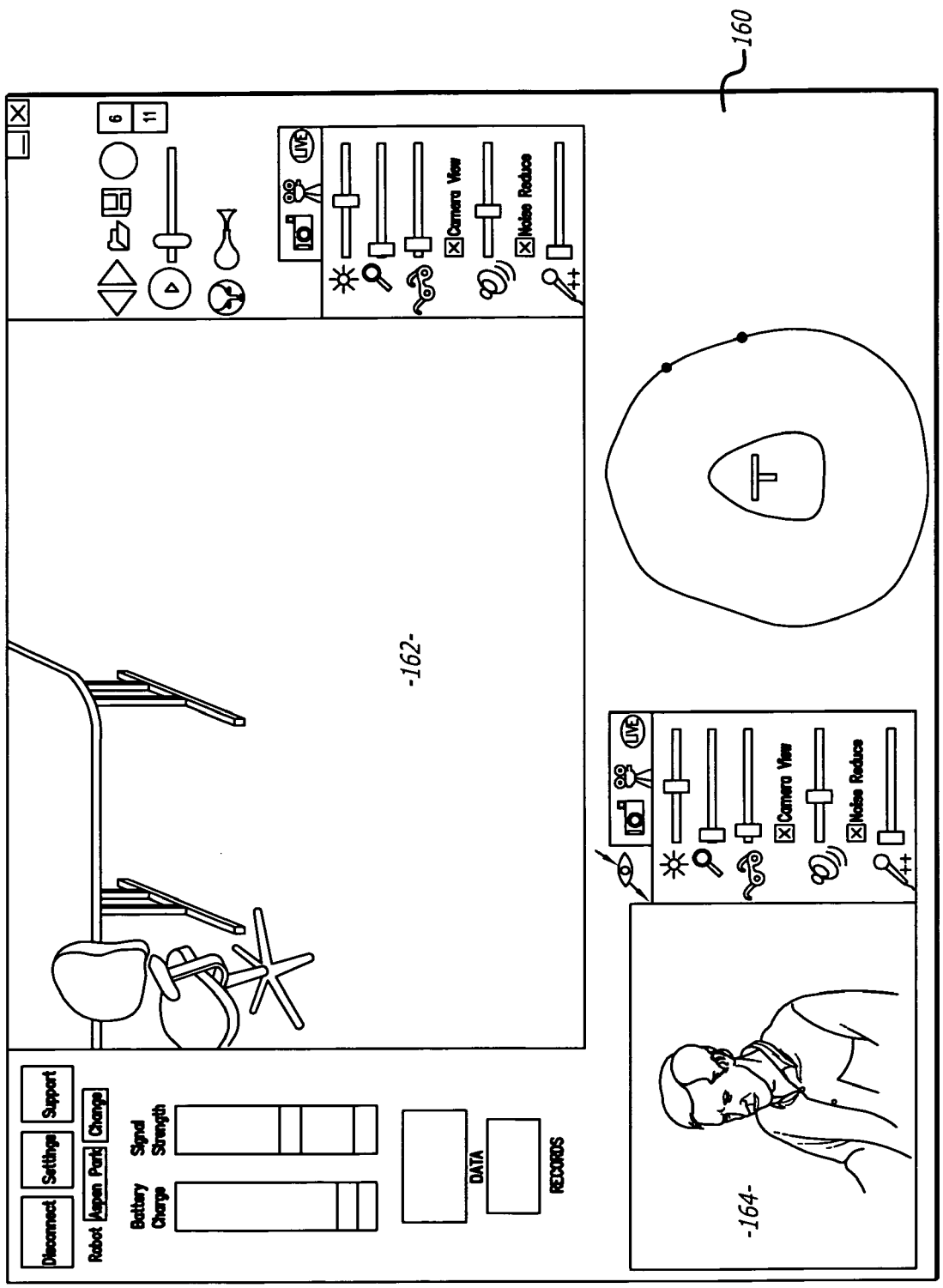
FIG. 5 is a graphical user interface at a remote station.

FIG. 5 shows a display user interface ("DUI") 160 that can be displayed at the remote station 14. The DUI 160 may include a robot view field 162 that displays a video image captured by the camera of the robot. The DUI 160 may also include a station view field 164 that displays a video image provided by the camera of the remote station 14. The DUI 160 may be part of an application program stored and operated by the computer 22 of the remote station 14.

Figures 6, 7:
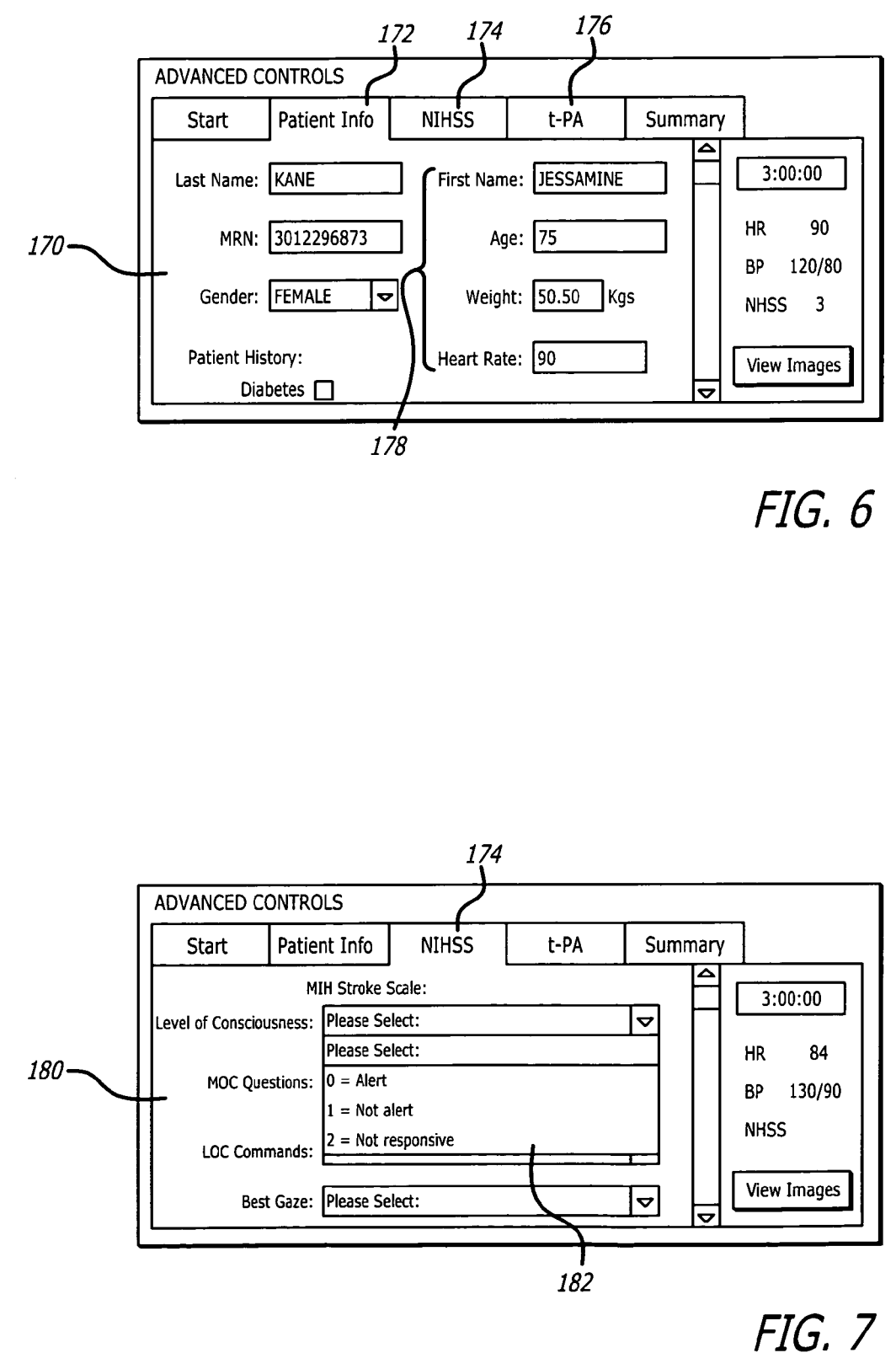

FIG. 6 shows a graphical user interface 170 that is displayed by the monitor of the remote station 16. The interface 170 includes a "PATIENT INFO" tab 172, a "NIHSS" tab 174 and a "t-PA" tab 176. Selection of the PATIENT INFO tab 172 displays various data fields 178 including patient name, age, weight, heart rate, etc. This may be the same information through the user interface.

FIG. 7 shows an interface 180 when the "NIHSS" tab 174 is selected. The interface 180 has a data field 182 that provides a questionnaire to rate the severity of a stroke victim using the NIHSS stroke scale. This provides a readily available medical tool for the physician.

Figure 8:
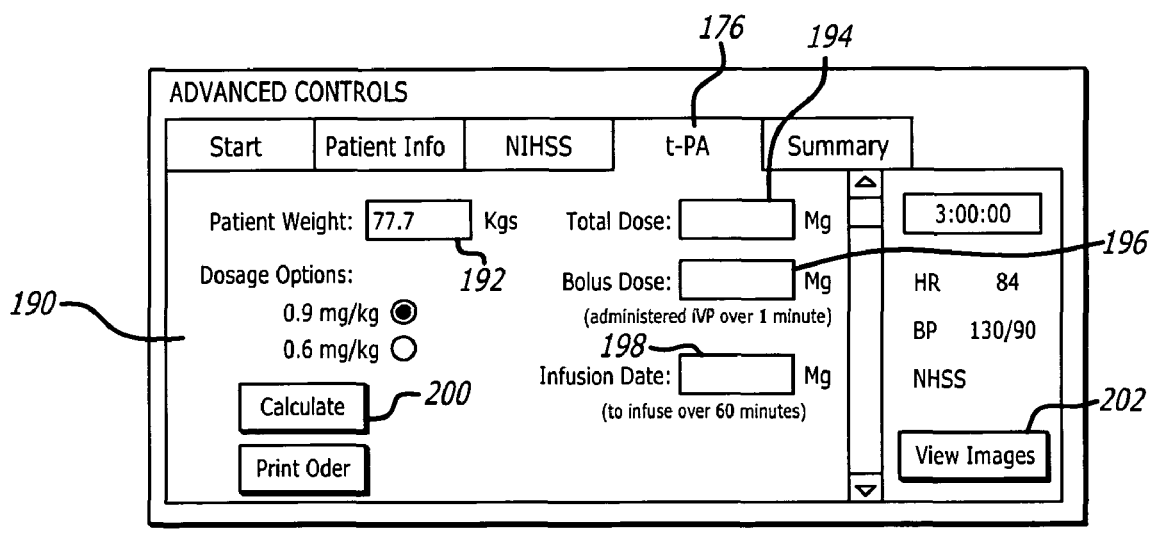
FIG. 8 is a graphical user interface displayed when a t-PA table is selected
Figure 9:
FIG. 9 is a graphical user interface displayed when a view images button is selected.

FIG. 8 shows an interface 190 when the "t-PA" tab 176 is selected. The interface 190 may include a data field 192 that provides the patient's weight, a "TOTAL DOSE" data field 194, a "BOLUS DOSE" data field 196 and an "INFUSION DOSE" data field 198. The interface 190 may also include a "CALCULATE" button 200. When the CALCULATE button 182 is selected the data fields 194, 196 and 198 are automatically populated with a calculated dosage. This provides a patient management plan for the physician to review. The interfaces 170, 180 and 190 also have a "VIEW IMAGES" button 202 that when selected displays an interface 210 shown in FIG. 9. The interface 210 includes a data field 212 and an image field 214. The image field 214 can provide a plurality of medical images such as a CT scan of the patient's head.

The system is useful for allowing a physician to remotely view and treat a stroke patient. The system provides patient information, NIHSS stroke severity assessment, calculated t-PA dosage and CT head images that allow the physician to provide real time remote patient treatment.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A robotic system, comprising:
   a mobile robot that has a camera and is located at a robot site;
   a user interface that is located at the robot site and allows medical information to be entered by a user; and,
   a remote station that is coupled to said mobile robot to control movement of said mobile robot, said remote station includes a monitor that is coupled to said mobile robot camera, and displays a graphical user interface that provides said medical information.

2. The system of claim 1, further comprising a records server that is coupled to said remote station and said user interface and stores said medical information.

3. The system of claim 1, further comprising an image server that is coupled to said remote station and stores a plurality of medical, images.

4. The system of claim 2, wherein said medical information includes patient statistics.

5. The system of claim 1, wherein said remote station provides a medical tool.

6. The system of claim 1, wherein said remote station provides a graphical user interface that can receive information and display a patient management plan.

7. The system of claim 6, wherein said medical tool is a stroke evaluation.

8. The system of claim 1, wherein said user interface is a computer terminal.

9. The system of claim 1, wherein said mobile robot includes a monitor coupled to a camera of said remote station.

10. The system of claim 9, wherein said mobile robot includes a speaker and a microphone.

11. A robotic system, comprising:
    a mobile robot that has a camera;
    a user interface that allows patient information and patient statistics to be entered by a user;
    a remote station that is coupled to said mobile robot to control movement of said mobile robot, said remote station includes a monitor that is coupled to said mobile robot camera, and that displays a plurality of graphical user interfaces, said graphical user interfaces provide said patient statistics, a medical tool and a patient management plan.

12. The system of claim 11, further comprising a records server that is coupled to said remote station and said user interface and stores said patient information and said patient statistics.

13. The system of claim 11, further comprising an image server that is coupled to said remote station and stores a plurality of medical images.

14. The system of claim 13, wherein at least one of said graphical user interfaces displays at least one of said medical images.

15. The system of claim 11, wherein said user interface is a computer terminal.

16. The system of claim 11, wherein said mobile robot includes a monitor coupled to a camera of said remote station.

17. The system of claim 16, wherein said mobile robot includes a speaker and a microphone.

18. A method for treating a patient, comprising:
    moving a mobile robot into a vicinity of a patient at a robot site through commands from a remote station;
    viewing the patient at the remote station through a camera of the mobile robot;
    entering information about the patient through a user interface located at the robot site;
    displaying the patient information at the remote station; and,
    displaying a patient management plan at the remote station.

19. The method of claim 18, further comprising displaying a medical image at the remote station.

20. The method of claim 18, wherein the patient management plan includes a calculated dosage at the remote station.

21. The method of claim 18, wherein the patient management plan is a stroke evaluation.

22. A graphical user interface that is displayed on a monitor of a remote station that controls a mobile robot, the mobile robot having a camera, comprising:
    a graphical user interface that includes;
      a patient information area;
      a medical assessment area; and,
      a patient management plan area.

23. The user interface of claim 22, wherein selection within said medical assessment area causes a display of a NIHSS scale questionnaire.

24. The user interface of claim 22, wherein selection within said patient management plan area causes a display with input fields and a calculation button that provides a calculated dosage when selected.

* * * * *